United States Patent
Sogan et al.

(10) Patent No.: US 7,403,283 B2
(45) Date of Patent: Jul. 22, 2008

(54) DETECTING MINORITY GASEOUS SPECIES BY LIGHT-EMISSION SPECTROSCOPY

(75) Inventors: Gloria Sogan, Epagny (FR); Julien Bounouar, Annecy-le-Vieux (FR); Jean-Pierre Desbiolles, Cruseilles (FR); Isabelle Gaurand, Annecy le Vieux (FR)

(73) Assignee: Alcatel, Paris (FR)

(*) Notice: Subject to any disclaimer, the term of this patent is extended or adjusted under 35 U.S.C. 154(b) by 402 days.

(21) Appl. No.: 11/064,484

(22) Filed: Feb. 24, 2005

(65) Prior Publication Data
US 2005/0190364 A1    Sep. 1, 2005

(30) Foreign Application Priority Data
Feb. 26, 2004    (FR) .................................... 04 50353

(51) Int. Cl.
*G01J 3/30*    (2006.01)
(52) U.S. Cl. ...................................... 356/316
(58) Field of Classification Search ...................... None
See application file for complete search history.

(56) References Cited

U.S. PATENT DOCUMENTS

| | | | |
|---|---|---|---|
| 3,836,255 A * | 9/1974 | Schuman | 356/311 |
| 5,014,217 A | 5/1991 | Savage | |
| 5,658,423 A | 8/1997 | Chou et al. | |
| 5,706,082 A * | 1/1998 | Colgan et al. | 356/311 |
| 5,991,020 A | 11/1999 | Loge | |
| 6,046,796 A | 4/2000 | Cheng et al. | |
| 6,157,867 A | 12/2000 | Cho et al. | |

FOREIGN PATENT DOCUMENTS

| | | |
|---|---|---|
| EP | 0584676 A1 | 3/1994 |
| EP | 6 77 737 A | 10/1995 |
| WO | WO 02/44698 A | 6/2002 |

OTHER PUBLICATIONS

U.S. Appl. No. 11/064,483, entitled "Detecting Gaseous Species by Light-Emission Spectrometry with Spectrum Processing.".

* cited by examiner

*Primary Examiner*—Tu T Nguyen
(74) *Attorney, Agent, or Firm*—Sughrue Mion, PLLC

(57) ABSTRACT

A method and apparatus for detecting minority gaseous species in a mixture by light-emission spectroscopy by means of an optical spectrometer (8), in which the radiation emitted by a plasma (4) present in the gas mixture for analysis is used and, in the spectrum of the radiation, lines are identified of a majority gaseous species that present amplitudes that are sensitive to the presence of a minority species, and information about the concentration of a minority gaseous species is deduced from the amplitude(s) of the sensitive line(s). This makes it possible to monitor minority gaseous species in real time.

21 Claims, 5 Drawing Sheets

DETECTING MINORITY GASEOUS SPECIES BY LIGHT-EMISSION SPECTROSCOPY

BACKGROUND OF THE INVENTION

The present invention relates to detecting gaseous species in a mixture by light-emission spectroscopy.

In order to detect gaseous species, recourse has already been made to light-emission spectroscopy, in which use is made of the light radiation emitted by a plasma present in the gas mixture for analysis, the optical spectrum of said radiation emitted by the plasma is measured, and the optical spectrum is analyzed in order to deduce therefrom the presence of gaseous species in the mixture.

The conventional method used for the step of analyzing the optical spectrum consists in viewing the optical spectrum in real time and in comparing it with spectra published in scientific libraries and established for each gaseous species. The method relies on the fact that each gaseous species generates light radiation of spectrum that is characteristic when it reaches a level of excitation causing it to emit light. Scientific libraries thus contain the light-emission spectra for each gaseous species. Each spectrum is constituted by a curve plotting light intensity values as a function of wavelength over the wavelength range constituting light radiation, i.e. in the ultraviolet, in the visible spectrum, and in the infrared. Generally, the light-emission spectrum of a gaseous species is a jagged curve presenting a large number of peaks or "lines". Each line is characterized by the wavelength and by the intensity of the light radiation and/or wavelength.

In known apparatuses, the light-emission spectrum is generally viewed by means of a computer which scans through the data issued by an optical spectrometer. Software associated with the spectrometer usually makes it possible to act on the integration time of the signal coming from the spectrometer, and thus on the intensity of the spectrum. The software may also act on the number of spectra to be averaged prior to display, thus making it possible to reduce noise. The software then allows the instantaneous light-emission spectrum to be viewed, and allows the variation in the amplitude of certain lines to be tracked, in order to deduce changes in the presence of a gas. The amplitude of a line at a defined wavelength generally makes it possible, when the gas is on its own, to track variation in the quantity of said gas that is present. The software also makes it possible to perform a certain number of mathematical operations such as subtracting spectra.

The light spectra of a gas mixture is generally constituted by the combination of the lines in the spectra that are specific to the various gaseous species present in the mixture.

It is sometimes possible, from the amplitudes of the lines of each specific spectrum, to deduce a measurement for the concentration of the corresponding gaseous species present in the mixture.

Measuring the concentrations of gaseous species in a mixture is quite easy and reliable when the gaseous species being sought out are easy to excite in the plasma. Such gaseous species that are easily excitable produce a light-emission spectrum having lines that can easily be seen and measured.

However, such a measurement of concentration becomes much more difficult for gaseous species that are more difficult to excite, particularly when those species are minority gaseous species, i.e. present in the mixture at a minority proportion only. Measuring the concentration of such poorly excitable or minority gaseous species in a mixture is possible at present only with measurement devices that are expensive, bulky, and difficult to operate, such as a mass spectrometer or a Fourrier transform infrared spectrometer (FTIR). For example, it is necessary to use such devices in order to measure traces of moisture in a vacuum in gas mixtures leaving a vacuum chamber in the semiconductor industry. Moisture is then present at a concentration of only a few thousands of parts per million (ppm). The cost of such measurements makes them economically unsuitable for use, particularly in methods of fabricating semiconductors.

The use of simpler spectroscopic measurement devices has not been envisaged for tracking traces of moisture. The difficulty comes in particular from the fact that the excitation of a gas in a plasma can vary strongly depending on the nature of the gas, and depending on whether the gas is alone or present in a gas mixture with other species.

For example, when considering moisture, the lines characteristic of the moisture to be observed (which moisture is present in only small quantity in the mixture) are poorly detectable or undetectable in the spectrum of the species that is present in a majority quantity, if it happens that that species is more easily excitable, as is the case for nitrogen. Tracking the lines characteristic of moisture, e.g. the hydrogen lines $H\alpha$, $H\beta$, and $H\gamma$, the oxygen line at about 777.3 nanometers (nm), and the OH line at about 306.8 nm, for example, is practically impossible in a gas mixture where other gases, such as nitrogen, are more easily excitable and take all of the available energy.

That is why gaseous species that are in a minority and/or that are difficult to excite, such as moisture, and that are present in the gas mixtures of flows extracted from vacuum chambers in the semiconductor industry have not, as a general rule, been detected in the past by conventional methods of light-emission spectroscopy.

SUMMARY OF THE INVENTION

The problem posed by the present invention is to avoid the drawbacks of prior art systems, in particular by making it possible in a manner that is reliable, fast, and inexpensive, to obtain an indication concerning the value of and the variation in the concentration of gaseous species that are in a minority and/or that are difficult to excite in a gas mixture under investigation, without having recourse to devices that are expensive, bulky, and difficult to operate.

The invention thus seeks to make it possible to track appropriately the presence of a species in a gas or a gas mixture by a conventional method of light-emission spectroscopy.

The invention applies in particular to tracking the composition of gas mixtures in vacuum chambers in the semiconductor industry, e.g. in process chambers, or in wafer transfer chambers.

The essential idea of the invention for this purpose is to seek out and use the influence that gaseous species that are in a minority and/or that are poorly excitable can have in a mixture on the spectrum lines that are characteristic of species that are in a majority and/or that are more easily excited in the mixture.

By doing this, the invention thus seeks to develop an indirect method of measuring the presence and the concentration of gaseous species that are difficult to excite, such as moisture.

The invention thus makes use of the observation whereby at least some of the characteristic lines of a gaseous species that is in a majority and/or that is easily excited, such as nitrogen, have amplitudes that vary as a function of the species that are in a minority and/or that are difficult to excite in the mixture, such as moisture.

It is therefore possible to track variation in species that are difficult to excite by light-emission spectroscopy, by analyzing the behavior of the amplitude of lines that are characteristic of a majority gaseous species, which are themselves sensitive to the presence of gases that are poorly excitable.

To achieve these objects and others, the invention thus provides a method of using light-emission spectroscopy to detect at least one gaseous species that is in a minority and/or difficult to excite in a mixture with at least one gaseous species that is in a majority and/or more easily excitable, in which a plasma is used in the gas mixture for analysis, and the original optical spectrum of the radiation emitted by the plasma is measured for subsequent comparison between the emitted spectrum and a library of known spectra, the method comprising a detection step that makes use, in the original spectrum, of one or more lines that are characteristic of the gaseous species in a majority and/or that is easily excitable, said line(s) being of amplitude that is sensitive to the presence of the species that is in a minority and/or that is difficult to excite, and information is deduced from the amplitude of said line(s) concerning the concentration of the gaseous species that is in a minority and/or that is difficult to excite.

The method may include a prior step of observing variations in the amplitudes of characteristic lines of the gaseous species that is in a majority and/or that is easy to excite as a function of variations in the concentration of the gaseous species that is in a minority and/or that is difficult to excite. To do this, in a flow that is preferably at constant pressure and that contains a gaseous species that is in a majority and/or easily excitable, varying quantities of a gaseous species that is in a minority and/or difficult to excite are introduced and the variations in the amplitudes of lines characteristic of the gaseous species that is in a majority and/or that is easily excitable are measured.

The prior observation step may advantageously be followed by a step of establishing a specific spectrum during which use is made, in the spectrum characteristic of the gaseous species that is in a majority and/or that is easily excitable, of sensitive lines, i.e. lines that present variations in amplitude as a function of variations in the concentration of the gaseous species that is in a minority and/or that is difficult to excite that are greater than a determined threshold.

It is these sensitive lines taken from the specific spectrum that are subsequently measured in amplitude, in order possibly to perform a sum, or an average, or any other mathematical treatment, that serves to improve the reliability or the sensitivity of the measurement. The result constitutes an image of the concentration of the gaseous species present in the mixture that is in a minority and/or that is difficult to excite.

Preferably, during a prior step, a calibration function is established and stored representing variation in the amplitude of the or each sensitive line as a function of the concentration of the gaseous species that is in a minority and/or that is difficult to excite.

The prior observation and detection steps are preferably performed using a total pressure for the gas mixture under observation that remains constant. This avoids errors that might result from any influence of pressure variations on the amplitudes of the lines.

If the method of the invention is to be implemented for measuring a gaseous species that is in a minority in a mixture whose pressure is likely to vary, it can be necessary to correct the measured amplitudes of the lines as a function of gas pressure. In a first implementation, lines are identified in the spectrum characteristic of the gaseous species that is in a majority and/or that is easily excitable, which lines have a combination, such as the average, that is insensitive to variations in the pressure of the mixture.

Alternatively, pressure calibration curves are established and are subsequently used for correcting the amplitude values of the lines as a function of pressure in order to deduce therefrom the quantity of a minority species that is actually present.

Preferably, the method includes a prior step of establishing a library of specific spectra containing at least one specific spectrum for each monitored gaseous species that is in a majority and/or that is easily excitable, said specific spectrum being obtained by spectral analysis of the gaseous species that is in a majority and/or that is easily excitable using the same measurement system as that which is to be used to implement the method, and said library is used for subsequent comparison with the spectrum of the mixture.

To do this, during the prior step, a gas flow containing the pure gas to be analyzed is caused to pass through the light spectrometer apparatus that is to be used, and the corresponding spectrum is stored. The energy distribution of the lines that are characteristic for a given gaseous species can change with the power of the source and with pressure. The library of spectra will thus serve as a database that is specific to the equipment being used.

If necessary, the library of spectra also stores calibration curves relating to the relationship between the amplitudes of the lines and gas pressure.

The method may advantageously be applied to detecting water vapor as the gaseous species in the mixture that is in a minority and/or difficult to excite.

The gaseous species that is in a majority and/or easy to excite may advantageously be nitrogen.

Nevertheless, the invention also applies to gaseous species that are in a minority and/or that are difficult to excite other than water vapor, and it is possible to use the lines characteristic of a gaseous species that is in a majority and/or that is easy to excite other than nitrogen.

In another aspect, the invention provides apparatus for implementing such a method of detecting gaseous species that are in a minority and/or that are difficult to excite, the apparatus comprising a plasma source for generating a plasma in the gas mixture under study, means for picking up and transmitting to an optical spectrometer the radiation emitted by the plasma, and a computer for analyzing the signals emitted by the optical spectrometer, the computer comprising a central unit and a program recorded in a program zone of a memory, said program comprising the sequence of instructions for implementing said method.

The plasma source may be either an external source such as the plasma source of a process chamber, or else a source integrated in the apparatus.

In an advantageous embodiment, the memory of the computer contains a library zone containing prerecorded specific optical spectra of gaseous species for analysis that are in a majority and/or easily excited, and a calibration function representing the variations in the amplitudes of sensitive lines as a function of the concentrations of gaseous species that are in a minority and/or that are difficult to excite.

BRIEF DESCRIPTION OF THE DRAWINGS

Other objects, characteristics, and advantages of the present invention appear from the following description of particular embodiments, given with reference to the accompanying figures, in which.

DETAILED DESCRIPTION OF THE INVENTION

Figure 1:
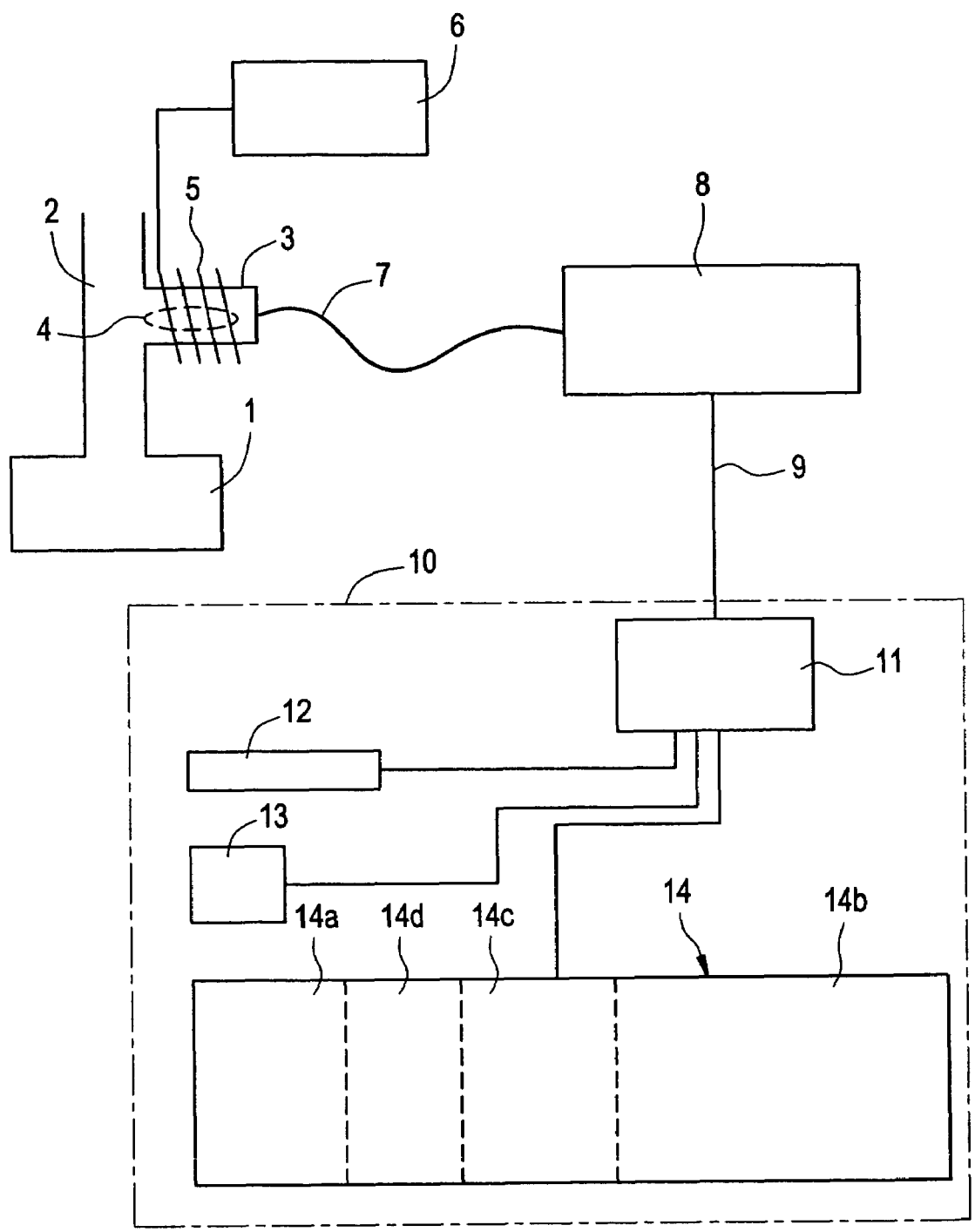
FIG. 1 is a diagram of a practical embodiment of apparatus of the present invention for detecting minority gaseous species.

In the embodiment shown in FIG. 1, the apparatus for detecting gaseous species in accordance with the invention is associated with equipment in which there flows a gas mixture for analysis. An example of such equipment comprises a vacuum chamber 1 which could be constituted in non-limiting manner by a process chamber or a transfer chamber as used in the fabrication of semiconductors, or of micro-electromechanical systems (MEMS). However, the apparatus can also be applied to any other equipment in which it is desired to analyze a gas mixture.

In FIG. 1, the gas mixtures leave the vacuum chamber 1 via a vacuum pipe 2.

In the vacuum pipe 2, or in a branch excitation enclosure 3, or indeed in the vacuum chamber 1, there is a zone in which the gas mixture is excited to form a plasma 4. By way of example, in the branch excitation enclosure 3, a plasma 4 is made by electromagnetic excitation by means of an exciter antenna 5 powered by a power generator 6. Examples consist in using a microwave generator, an inductively coupled plasma (ICP) type radio frequency (RF) generator, or any other suitable generator.

The light radiation emitted by the plasma 4 is picked up and transmitted to an optical spectrometer 8. Transmission may be performed by an optical fiber 7 or via a suitable connector, or via any other light transmission means.

In known manner, the optical spectrometer 8 generates signals that constitute an image of the detected light spectrum, and sends them over a line 9 to a computer 10.

The computer 10, which is shown diagrammatically, comprises a central unit 11 connected to input/output means 12 such as a keyboard, connected to display means 13 such as a screen, and connected to a memory 14.

The memory 14 contains a program zone 14a having programs recorded therein.

The memory 14 also contains a library zone 14b suitable for containing reference data, in particular known light spectra for pure gaseous species, and the calibration function.

The memory 14 contains a measurement memory zone 14c in which there can be recorded the data corresponding to raw light spectra received from the optical spectrometer 8.

The memory 14 contains a results memory zone 14d suitable for containing amplitude data concerning sensitive lines and concentrations of gaseous species.

The program zone 14a contains, in particular, a program for spectrum processing using the method of the invention.

Reference is made below to the light spectrum shown in FIG. 2 by way of example. It comprises a curve of light intensity plotted up the ordinate as a function of wavelength plotted along the abscissa. It can be seen that this curve, e.g. corresponding to a given gas mixture in which nitrogen constitutes a majority species, has a large number of peaks or "lines", i.e. zones that form maxima, and the same number of zones that corresponds to minima.

Figure 2:
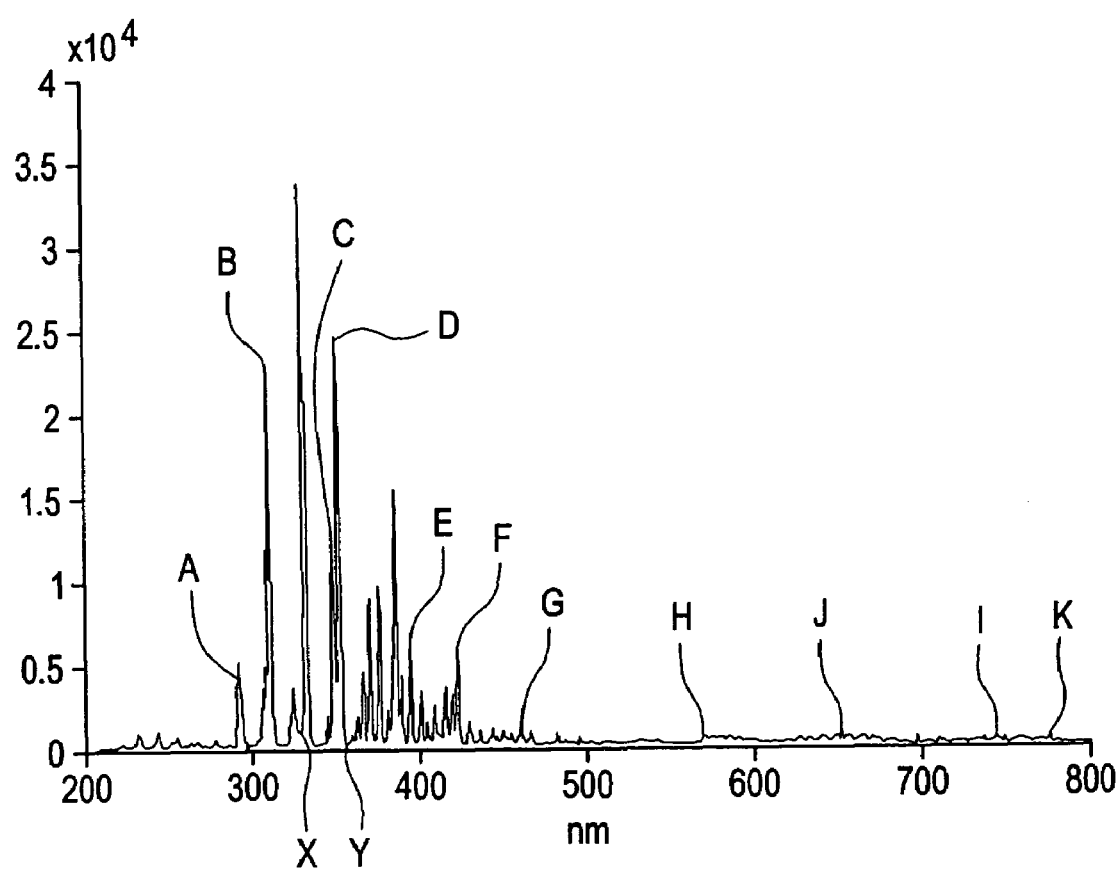
FIG. 2 is a light-emission spectrum of the kind that can be obtained from a light-emission spectrometer while analyzing a gas mixture, and taken by way of example.

In the mixture spectrum shown in FIG. 2, there can be seen for example, peaks or lines A, B, C, D, E, F, G, H, I, J, and K and minima such as X or Y.

By way of example, it is assumed that the lines B, C, D, F, G, J, and K are characteristic of the usual light-emission spectrum of a majority gaseous species of the mixture, e.g. nitrogen.

In the mixture, there is also a gaseous species that is in a minority and/or that is difficult to excite, such as moisture, and its lines are not clearly apparent in the spectrum of FIG. 2.

The method of the invention enables the concentration of moisture in the mixture to be characterized by analyzing lines that are characteristic of a majority gaseous species, i.e. by analyzing the lines B, C, D, F, G, J, and K.

To do this, a search is made amongst the lines B, C, D, F, G, J, and K for the or each line characteristic of nitrogen that is of an amplitude that is sensitive to the presence of a minority species in the mixture. Thus, with the apparatus of FIG. 1, a prior step is performed of observing variations in the amplitudes of the characteristic lines B, C, D, F, G, J, and K as a function of variations in the concentration of a minority gaseous species. In practice, a plurality of light-emission spectrometry measurements are performed on mixtures present in the vacuum pipe 2, while forcing the concentration of a minority gaseous species to vary. It is then found that certain lines that are characteristic of nitrogen present amplitudes that vary, whereas other lines present amplitudes that remain practically constant.

By way of example, it is assumed that amplitude variation is observed for lines B, C, F, and J, while lines D, G, and K remain insensitive.

Consequently, it is possible from the amplitudes of all or some of the lines B, C, F, and J in the FIG. 2 mixture spectrum to deduce information concerning the concentration of a minority gaseous species, even if the lines that are characteristic of a minority gaseous species are not themselves visible in the spectrum.

Thus, at the end of the prior observation step, a specific spectrum is established and recorded in the library memory zone 14b, which specific spectrum comprises only those spectrum lines characteristic of a majority gaseous species that are also sensitive to the presence of a minority gaseous species, i.e. lines that present variations in amplitude as a function of variation in the concentration of a minority gaseous species, where such variation is greater than a determined threshold so as to give satisfactory sensitivity to the measurement method of the invention.

Preferably, during the prior step of observing variations in amplitude, a calibration function is established and recorded, which function is representative of the amplitude variation of the sensitive line(s) as a function of the concentration of a minority gaseous species.

For example, this calibration function can be a table containing the amplitude values for the lines B, C, F, and J, together with the corresponding values for the concentration of a minority gaseous species that has been voluntarily injected into the vacuum pipe 2 during the prior step of observing variations in amplitude.

In the invention, it is important to perform the prior step of observing variations in amplitude using the apparatus such as that shown in FIG. 1 that will subsequently be used for performing the measurements of the concentrations of minority gaseous species.

The emission of characteristic lines in the spectrum depends on various parameters of the apparatus, and in particular on the power of plasma generation, on geometrical characteristics of the apparatus, and on the sensitivity of the optical spectrometer. By using the same measurement conditions, the same characteristic lines of the spectrum are generated.

A prior step is performed of setting up a library of specific spectra containing at least one specific spectrum for each majority gaseous species to be monitored. This specific spectrum is obtained by analyzing the spectrum of a majority gaseous species using the same measurement system that is to be used for implementing the method, and said library is subsequently used for comparison with the spectrum of the mixture.

By way of example, the software can base measuring concentration either on measuring the intensity of one of the characteristic lines B, C, F, and J, or on the mean emission intensity of the four sensitive lines B, C, F, and J, or on the sum of the intensities, or on the result of any other suitable mathematical treatment performed on the intensities of the lines. It is then possible to display variation in a minority gaseous species as represented by variation in the mean or the total intensity of the sensitive lines B, C, F, and J.

Variation in all or some of the sensitive characteristic lines B, C, F, and J can be tracked quickly, thus making it possible to monitor the concentration of a minority gaseous species in real time.

Amongst the lines B, C, F, and J of a majority gaseous species that are sensitive to the presence of a minority gaseous species, it is generally found that some of the lines such as the lines B, C, and F are also sensitive to the pressure of the gas in which inspection is being performed, whereas other lines of a majority gaseous species, such as the line J, can be insensitive to pressure, at least in certain pressure ranges.

Likewise, some of the lines may be sensitive to pressure in a manner that is monotonic, i.e., for example, increasing over the entire zone of variation, whereas other lines may present variation that is not monotonic.

Figure 3:
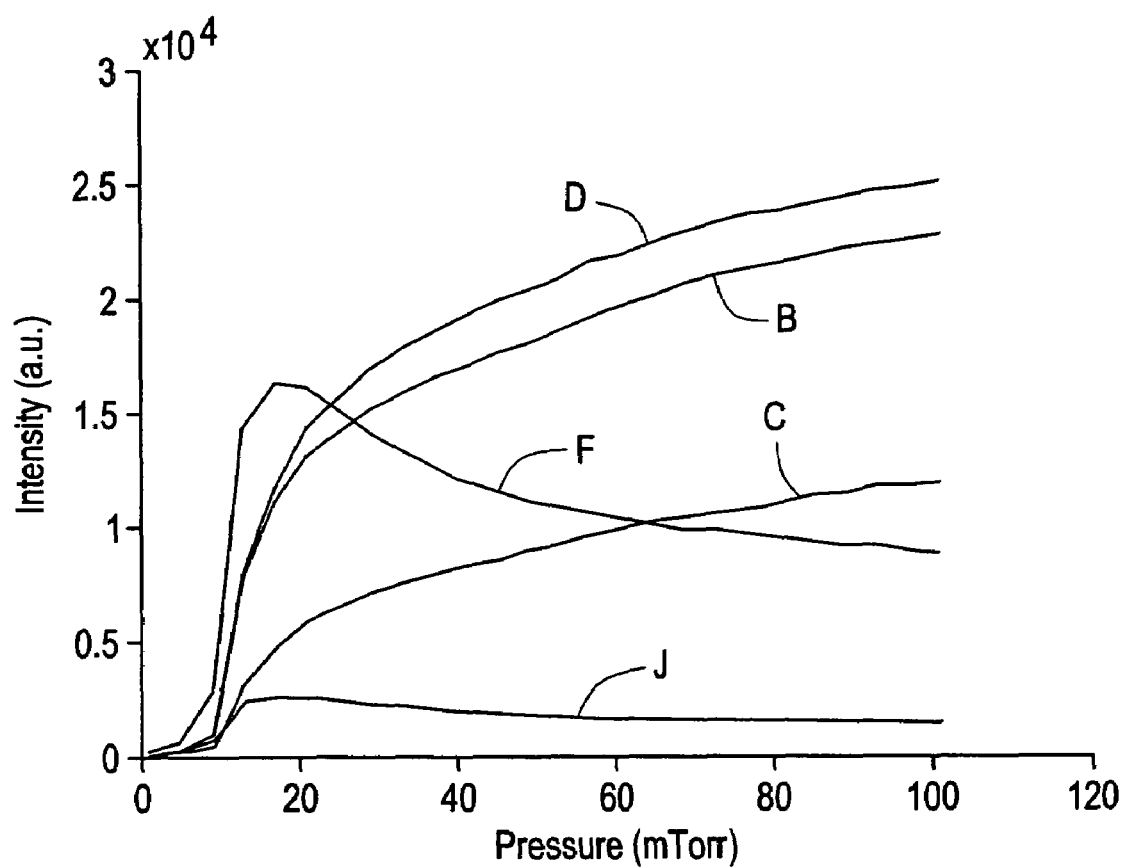
FIG. 3 shows variations in the intensities of certain spectrum lines as a function of pressure.

These phenomena are shown in FIG. 3. This figure shows the variation in the intensity of certain sensitive characteristic lines of a majority species as a function of the pressure of the gas mixture. The line B varies monotonically, increasing continuously with increasing pressure. The same applies to the line C, but with variation that is somewhat slower. The line D also varies by increasing continuously, and its rate of increase is even faster, however it is not used since it is not sensitive to the presence of a minority species. The line F is of intensity that increases strongly in the low pressure zone, after which it reaches a maximum and subsequently falls off progressively with increasing pressure. The line J follows a curve that is similar but flatter, rising less quickly followed by a peak and falling off slowly and almost imperceptibly.

For example, it can be assumed that in the pressure range 20 millitorr (mTorr) to 100 mTorr, the line J is practically insensitive to pressure. It would thus be possible to take the line J on its own into consideration in order to deduce therefrom a good evaluation of the quantity of a minority species present in the mixture, independently of the pressure of the mixture.

However, the quantity of a minority species in the mixture can be evaluated using any of the sensitive lines B, C, and F providing the pressure of the gas mixture is also known simultaneously.

For this purpose, it is possible in the invention to make use of a spectrum line, where such a line exists, that is sensitive to pressure in monotonic manner like the lines B and C, and that is simultaneously insensitive to the presence of a minority species. This applies, for example, to the line D which varies monotonically as a function of pressure, as shown in FIG. 3, but which is not found to be sensitive to the presence of a minority species. By considering the amplitude of the line D, it is therefore possible to deduce the pressure of the mixture. Thereafter, knowing the pressure, the quantity of a minority species can be deduced from the amplitudes of the other lines B, C, F, and J which are sensitive to the presence of a minority species.

For certain majority species in the presence of certain minority species, it can happen that there is no line that is insensitive to pressure and simultaneously there is no line that is insensitive to the presence of a minority species. Under such circumstances, the effect of pressure variations can be compensated by seeking lines that are simultaneously less sensitive to pressure variations and sensitive to the presence of minority species, by combining the amplitudes of such lines so as to determine an average that does not vary perceptibly as a function of pressure. Such processing thus makes it possible to obtain a signal that is sensitive to moisture without being sensitive to pressure. The intensities of the lines that vary positively relative to pressure compensate for any variations in the intensities of lines that vary negatively relative to pressure, so as to obtain a signal that does not vary with variations in pressure. Such a signal depends solely on the quantity of a minority species, and it is thus possible to deduce a good evaluation for the quantity of a minority species in the mixture. For example, in FIG. 3, it is possible to combine lines B and F of nitrogen over the pressure range extending from 20 mTorr to 100 mTorr.

In practice, it is generally possible to consider regions of a majority species spectrum that are sensitive to the presence of a minority species, and regions of the spectrum that are sensitive to pressure.

Figure 4:
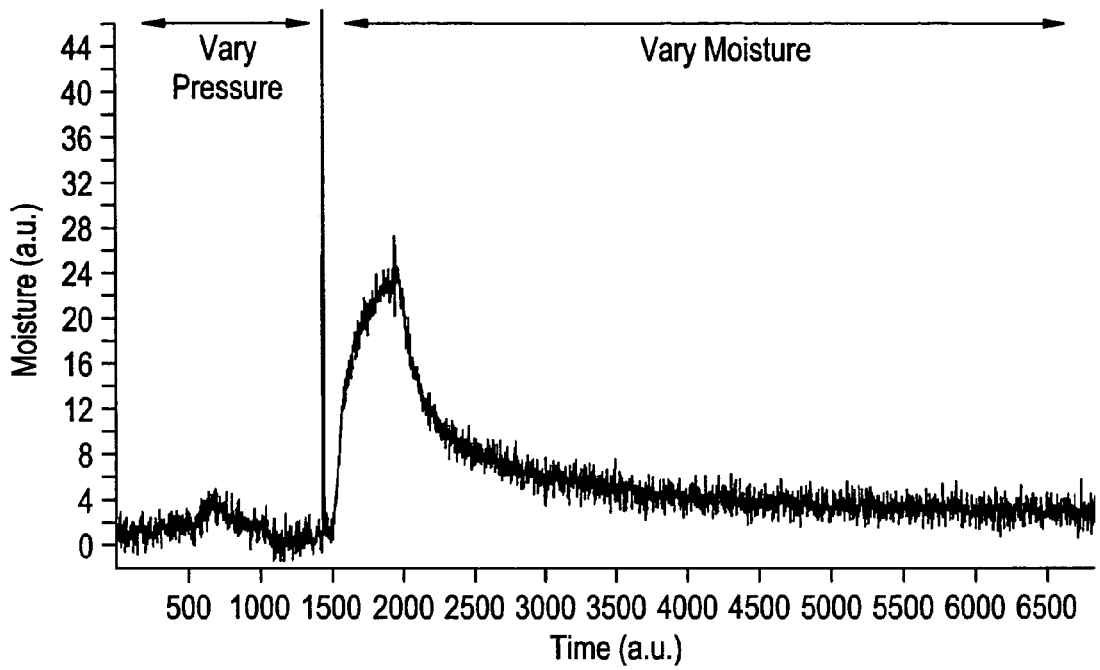
FIGS. 4 and 5 show variations in the intensities of certain spectral regions following disturbances in pressure or in moisture.

For example, in the spectrum of nitrogen, the region of the spectrum extending from 718 nm to 728 nm is sensitive to pressure, as can be seen in FIG. 4: during an initial time period, extending from 0 to 1500 arbitrary time units, the gas pressure of the mixture was caused to vary, and the mean of the intensities of the regions under consideration in the spectrum remained substantially constant. In a second time period extending from 1500 to 6500 arbitrary time units, moisture content was caused to vary, and the intensity curve varied accordingly.

Figure 5:
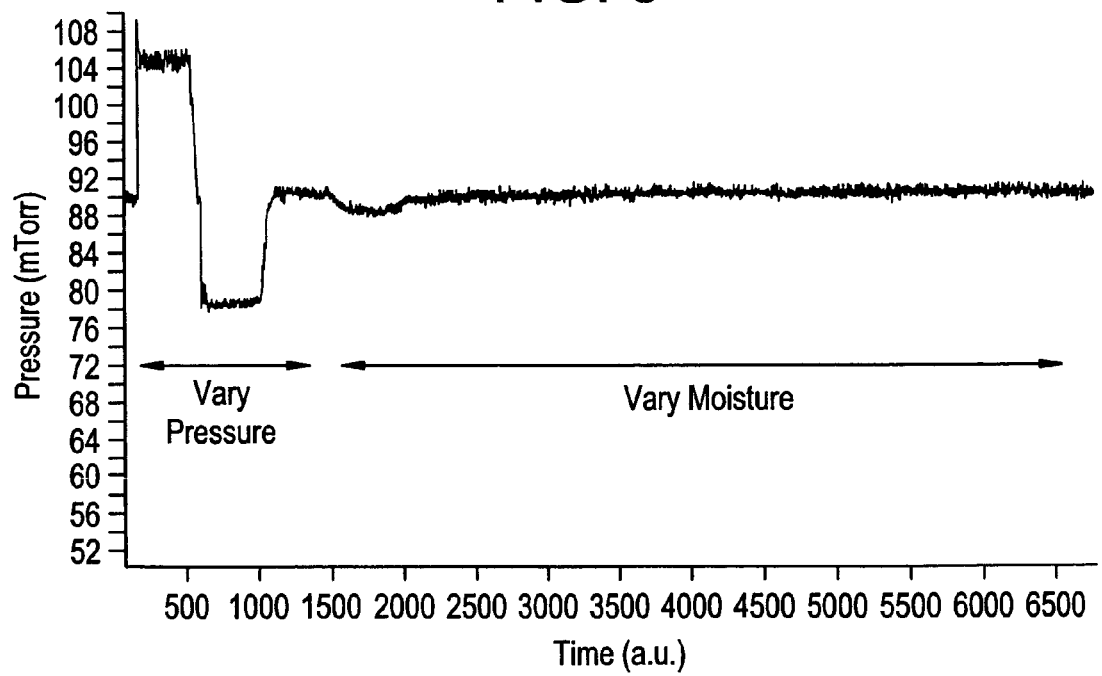

When considering the region of the spectrum extending from 773 nm to 781 nm, the curve shown in FIG. 5 is obtained, likewise for variation in pressure followed by variation in moisture. This curve shows that this region of the nitrogen spectrum is sensitive to pressure and practically insensitive to the presence of moisture.

Figure 6:
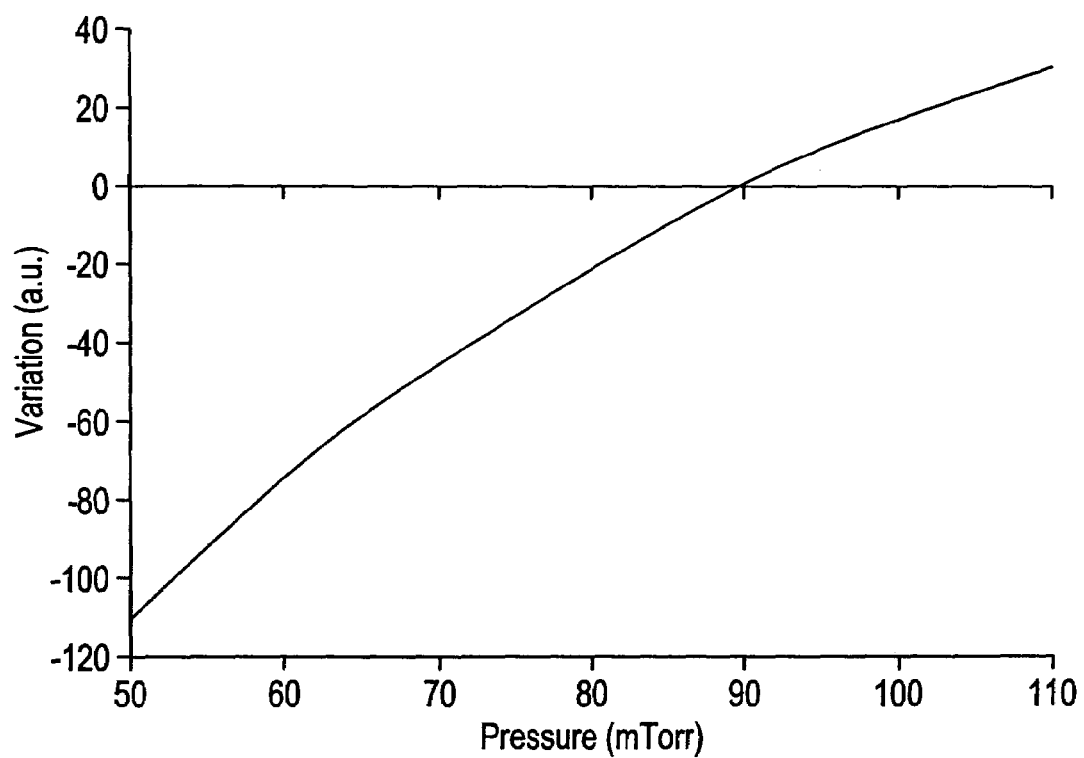
FIG. 6 is a curve for calibrating the intensity of a line as a function of pressure.

Another way of correcting the influence of pressure on measuring the quantity of a minority gaseous species is shown in FIG. 6. This involves establishing a calibration curve relative to pressure by determining, during prior testing, how the amplitude of one or more lines varies as a function of pressure around the mean pressure that is generally to be found in the mixture while it is being measured. In the example of FIG. 6, amplitude has been calibrated as a function of pressure about a mean pressure of about 90 mTorr. Thereafter, by knowing the pressure as given by some other sensor or by some other means of evaluating pressure, it is possible to correct the measured line amplitude(s) using the values given by the calibration curve, and then to deduce the exact value of the quantity of a minority species that corresponds to the correct amplitude value.

Tracking can be applied to a plurality of species of equipment in parallel that operate in similar manner, and comparisons can be performed in order to detect possible faults on any piece of equipment.

To do this, a reference is initially established for each piece of equipment. The signatures as obtained in this way then enable different species of equipment to be compared, and thus to determine whether a parameter of any one piece of equipment has changed.

This method can be particularly useful after action has been taken on a piece of equipment, e.g. when it has been put back into production. Data relating to a minority gaseous species can also be associated with other data coming from the equipment. The purpose is to obtain a population of reference data for that piece of equipment.

Thereafter, by monitoring the equipment in real time it is possible to detect faults by statistical processing. The origin of a fault can then be interpreted as a function of previously-identified signatures of faults that have already occurred.

The advantage of the invention then lies in providing information about what is actually occurring inside a piece of equipment, e.g. inside a process chamber, using means that are fast and inexpensive. It is then possible to refine the signature of the equipment using the new data in situ.

In practice, the invention can have multiple applications.

In a first example, it is possible to monitor the normal operating state of a piece of equipment through which the analyzed gas mixture is flowing, e.g. the state of the vacuum chamber 1. For this purpose, a minority gaseous species is selected that is representative of this normal operating state of the equipment 1. Variation in said selected minority gaseous species is then monitored in real time, with said variation being compared with reference variation data, and a warning or a control signal is generated when the data diverges from the reference data.

One application of this example lies in monitoring the leakage properties of the equipment 1. Concerning inward leaks from the outside atmosphere, the presence of traces of moisture can be sought in the equipment 1, together with variations thereof, or more generally a search can be made for the presence of and any variation in that presence of any minority species that is representative of a leak, i.e. that ought not to be present in the equipment 1 but that is present outside it. This presence of moisture inside the equipment 1 then proves that a leak is present. The method of the invention provides great sensitivity in monitoring for such leaks, but it is inexpensive to implement.

Preferably, in the search for leaks, it is advantageous to compare the variation in time of traces of moisture, or any other minority species representative of leaks into the equipment 1, with the sequence of functional events in the equipment 1, in order to deduce the origins of variations in said variation of traces of moisture or any other minority species representative of leaks. For example, a sudden increase in the presence of moisture may be identified as being simultaneous with the opening of a door in the equipment, from which it can be deduced that the moisture came in not via a leak but by being put into communication with a moist atmosphere through the door. This phenomenon is shown by way of example in FIG. 4 where there can be seen a sudden increase in moisture starting from time unit 1500.

In practice, in apparatus for detecting minority gaseous species in accordance with the invention, when associated with equipment 1 into which leaks are to be detected, means are provided to synchronize the detection of a minority gaseous species representative of a leak with the operating events of the equipment 1 being monitored. These means for synchronizing detection can comprise the central unit 11 associated with a suitable subprogram, for example for displaying synchronously the variation in time of a minority species, e.g. as shown in FIG. 4, with operating events of the equipment 1 such as doors being opened, gases being injected, valves being opened or closed, and wafers being inserted or extracted.

An example of a particularly important application of the method of the invention lies in controlling wafer transfer chambers. Such control is made possible and inexpensive by the method of the invention and consists in monitoring variation in traces of moisture in a wafer transfer chamber. This makes it possible to detect problems that can involve the content of the transfer chamber, i.e. semiconductor wafers, before such wafers enter a new process chamber. This makes it possible to detect free or post-process contamination, if any, which contamination might significantly reduce the production yield and the performance of the equipment.

In a second example, the method of the invention is applied to detecting deviation in a process implemented in the equipment. To do this, a minority gaseous species is selected that is representative of the state of progress of the process using the gas mixture under analysis; the variation in said selected minority gaseous species is monitored in real time and said variation is compared with reference data for variation of the process, with a warning or control signal being generated in the event of a divergence away from the reference variation data for the process.

In another example, the measurement method of the invention is applied to monitoring the effectiveness with which an enclosure has been purged by purge gas. To do this, a minority gaseous species is selected that is representative of the state of progress of said purge by means of the purge gas, and a minority species is detected; variation in the content of said selected minority gaseous species is monitored in real time and said variation is compared with reference data for variation during purging, with a warning or control signal being generated when variation in the purge data reaches a state indicative of the end of purging, for example when a given threshold is reached that corresponds to the end of purging. By way of example, the purging of a chamber by means of nitrogen can be monitored, where the chamber previously contained chlorine. It is then possible to monitor the presence and the variation in the presence of chlorine, a minority species, in nitrogen which constitutes a majority species during purging.

In another example, the method of the invention for detecting minority gaseous species is applied to detecting the end of chamber reconditioning. Under such circumstances, a minority gaseous species is selected that is representative of the end of reconditioning a chamber that is being reconditioned; variation in the quantity of said selected minority gaseous species in said chamber that is being reconditioned is then monitored in real time, said variation is compared with reference data for variation during reconditioning of the chamber, e.g. by being compared with a given threshold, and a warning or control signal is generated when the data for said selected minority gaseous species reaches a state indicative of the end of chamber reconditioning, for example when a predetermined threshold is reached.

The present invention is not limited to the embodiments described explicitly above, but includes the various variants and generalizations that are within the competence of the person skilled in the art.

What is claimed is:

1. A method of using light-emission spectroscopy to detect at least one gaseous species that is in a minority and/or difficult to excite in a mixture with at least one gaseous species that is in a majority and/or more easily excitable, in which a plasma is used in the gas mixture for analysis, and an original optical spectrum of the radiation emitted by the plasma is measured for subsequent comparison between the emitted spectrum and a library of known spectra, the method comprising a detection step that makes use, in the original spectrum, of one or more lines that are characteristic of the gaseous species in a majority and/or that is easily excitable, said line(s) being of amplitude that is sensitive to the presence of the species that is in a minority and/or that is difficult to excite, and information is deduced from the amplitude of said line(s) concerning the concentration of the gaseous species that is in a minority and/or that is difficult to excite, wherein said method further comprising displaying said information.

2. A method according to claim 1, including prior to detecting the at least one gaseous species, observing variations in the amplitudes of characteristic lines of the gaseous species that is in a majority and/or that is easy to excite as a function of variations in the concentration of the gaseous species that is in a minority and/or that is difficult to excite.

3. A method according to claim 2, in which the observing step is followed by a step of establishing a specific spectrum during which use is made, in the spectrum characteristic of the gaseous species that is in a majority and/or that is easily excitable, of sensitive lines that present variations in amplitude as a function of variations in the concentration of the gaseous species that is in a minority and/or that is difficult to excite that are greater than a determined threshold.

4. A method according to claim 3, in which the observing and detection steps are performed at a total pressure that is constant.

5. A method according to claim 1, in which, a calibration function is established and stored representing variation in the amplitude of at least one sensitive line as a function of the concentration of the gaseous species that is in a minority and/or that is difficult to excite prior to the detecting.

6. A method according to claim 1, in which lines are identified in the spectrum characteristic of the gaseous species that is in a majority and/or that is easily excitable, which lines have a combination, such as the average, that is insensitive to variations in the pressure of the mixture.

7. A method according to claim 1, in which pressure calibration curves are established and are subsequently used for correcting the amplitude values of the lines as a function of pressure in order to deduce therefrom the quantity of a minority species that is actually present.

8. A method according to claim 1, including establishing a library of specific spectra containing at least one specific spectrum for each monitored gaseous species that is in a majority and/or that is easily excitable prior to said detecting, said specific spectrum being obtained by spectral analysis of the gaseous species that is in a majority and/or that is easily excitable using the same measurement system as that which is to be used to implement the method, and said library is used for subsequent comparison with the spectrum of the mixture.

9. A method according to claim 1, applied to detecting water vapor as the gaseous species that is in a minority and/or that is difficult to excite in a mixture.

10. A method according to claim 9, in which the gaseous species that is in a majority and/or that is easy to excite is nitrogen.

11. A method according to claim 1, in which the at least one minority gaseous species is selected that is representative of the normal operating state of a piece of equipment through which there flows the gas mixture under analysis, variation in said selected minority gaseous species is monitored in real time, said variation is compared with reference variation data, and a warning or control signal is generated in the event of a departure from the reference variation data.

12. A method according to claim 11, in which any leaks from the equipment are monitored by monitoring the presence and the variation of traces of moisture or any other minority species representative of leaks that ought not to be present in the equipment but that is present outside the equipment.

13. A method according to claim 12, applied to monitoring wafer transfer chambers.

14. A method according to claim 12, in which variation over time in traces of moisture or other minority species representative of leaks in the equipment is compared with the sequence of operating events of the equipment in order to deduce the origin of changes in said variation.

15. A method according to claim 1, in which a minority gaseous species is selected that is representative of the state of progress of a process implementing the gas mixture under analysis, variation in said selected minority gaseous species is monitored in real time, said variation is compared with reference variation data for the process, and a warning or control signal is generated in the event of departure from the reference variation data for the process.

16. A method according to claim 1, in which a minority gaseous species is selected representative of the state of progress in purging an enclosure with purge gas, and a minority species is detected, variation in said selected minority species over time is monitored, said variation is compared with reference variation data for purging, and a warning or control signal is generated when the purged variation data reaches a state indicative of the end of purging.

17. A method according to claim 16, in which the presence and variation of chlorine is monitored in the enclosure during purging with nitrogen.

18. A method according to claim 1, in which a minority gaseous species is selected that is representative of the reconditioning state of a chamber being reconditioned, the variation in said selected minority gaseous species in said chamber being reconditioned is monitored in real time, said variation is compared with reference variation data for chamber reconditioning, and a warning or control signal is generated when the data for said selected minority gaseous species reaches a state indicative of the end of chamber reconditioning.

19. Apparatus for implementing a method of detecting gaseous species that are in a minority and/or that are difficult to excite according to claim 1, the apparatus comprising a plasma source for generating a plasma in the gas mixture under study, means for picking up and transmitting to an optical spectrometer the radiation emitted by the plasma, and a computer for analyzing the signals emitted by the optical spectrometer, the computer comprising a central processing unit and a program recorded in a program zone of a memory, said program comprising the sequence of instructions for implementing said method.

20. Apparatus according to claim 19, in which the memory of the computer contains a library zone containing prerecorded specific optical spectra of gaseous species for analysis that are in a majority and/or easily excited, and a calibration function representing the variations in the amplitudes of sensitive lines as a function of the concentrations of gaseous species that are in a minority and/or that are difficult to excite.

21. Apparatus according to claim 19, associated with equipment in which leaks are to be detected, the apparatus including means for synchronizing detection of a minority gaseous species representative of leaks with operating events of the equipment.

* * * * *